US011830713B2

(12) United States Patent
Dang et al.

(10) Patent No.: US 11,830,713 B2
(45) Date of Patent: Nov. 28, 2023

(54) METHOD FOR SIMULTANEOUS DETERMINATION OF PARTICLE SIZE DISTRIBUTION AND CONCENTRATION OF NANOPARTICULATE MERCURY IN NATURAL SOILS

(71) Applicant: INSTITUTE OF SOIL SCIENCE, CHINESE ACADEMY OF SCIENCES, Nanjing (CN)

(72) Inventors: Fei Dang, Nanjing (CN); Yujun Wang, Nanjing (CN); Weiping Cai, Nanjing (CN)

(73) Assignee: INSTITUTE OF SOIL SCIENCE, CHINESE ACADEMY OF SCIENCES, Nanjing (CN)

( * ) Notice: Subject to any disclaimer, the term of this patent is extended or adjusted under 35 U.S.C. 154(b) by 51 days.

(21) Appl. No.: 17/745,203

(22) Filed: May 16, 2022

(65) Prior Publication Data

US 2023/0095510 A1    Mar. 30, 2023

(30) Foreign Application Priority Data

Sep. 24, 2021    (CN) .......................... 202111122320.0

(51) Int. Cl.
| | |
|---|---|
| *H01J 49/00* | (2006.01) |
| *G01N 15/02* | (2006.01) |
| *G01N 33/24* | (2006.01) |
| *H01J 49/04* | (2006.01) |
| *H01J 49/10* | (2006.01) |

(52) U.S. Cl.
CPC .......... *H01J 49/0031* (2013.01); *G01N 15/02* (2013.01); *G01N 33/24* (2013.01); *H01J 49/0459* (2013.01); *H01J 49/105* (2013.01)

(58) Field of Classification Search
CPC .. H01J 49/0031; H01J 49/0459; H01J 49/105; G01N 15/02; G01N 15/0656; G01N 15/1031; G01N 15/06; G01N 33/24; G01N 23/04; G01N 23/20091; G01N 27/626; G01N 21/6404; G01N 2015/1043
USPC ....................................................... 250/282
See application file for complete search history.

(56) References Cited

U.S. PATENT DOCUMENTS

2015/0239788 A1* 8/2015 Yamashita ............... C05B 19/00
                                                                    504/101
2022/0413166 A1* 12/2022 Saccomanno .......... A23B 7/015

* cited by examiner

*Primary Examiner* — Kiet T Nguyen
(74) *Attorney, Agent, or Firm* — DeLio Peterson & Curcio LLC; Robert Curcio

(57) ABSTRACT

Disclosed is a method for simultaneous determination of particle size distribution, concentrations of nanoparticulate mercury (Hg-NPs) in natural soils. The method uses sodium pyrophosphate as the extractant, and allows quick extraction of Hg-NPs in the soil without dissolution or aggregation. In combination with spICP-MS determination, the method makes it possible to simultaneously determine the particle size distribution and concentration of Hg-NPs in the complex soil matrix, with accurate determination results.

12 Claims, 15 Drawing Sheets

METHOD FOR SIMULTANEOUS DETERMINATION OF PARTICLE SIZE DISTRIBUTION AND CONCENTRATION OF NANOPARTICULATE MERCURY IN NATURAL SOILS

CROSS REFERENCE TO RELATED APPLICATION

This patent application claims the benefit and priority of Chinese Patent Application No. 202111122320.0, filed on Sep. 24, 2021, the disclosure of which is incorporated by reference herein in its entirety as part of the present application.

TECHNICAL FIELD

The present disclosure relates to the technical field of substance determination, and in particular to a method for simultaneous determination of particle size distribution and concentration of nanoparticulate mercury (Hg-NPs) in natural soils.

BACKGROUND ART

Methylmercury (MeHg) is a neurotoxin and its production is largely determined by the forms of inorganic mercury in the environment. Particulate mercury accounts for more than 70% of inorganic mercury in soil, and is considered to be inert for methylation. As a result, the conversion of inorganic mercury to particulate mercury is regarded as the most promising strategies for remediation of mercury-contaminated soil. However, laboratory experiments with pure cultures have recently demonstrated that nanoparticulate mercury (Hg-NPs; 1-100 nm) could be methylated by microorganisms, and its methylation potential could be comparable to ionic mercury. Unfortunately, the exposure level of indigenous Hg-NPs in natural soils remains largely unknown. The lack of this knowledge hampers our understanding of on the biochemical processes of Hg-NPs in soil, and restricts further application of the remediation strategies. Therefore, quantifying Hg-NPs in soils has theoretical and practical urgency.

Chemical identification of target Hg-NPs in complex soil matrices is not straightforward. Quantitative information of Hg-NPs includes not only the mass concentration, but also their particle size distribution and particle concentrations. Especially, the low ambient Hg concentrations ($\mu g \cdot kg^{-1}$) in soil, background interferences of heterogeneous soil components, and variable mercury species in soil samples make Hg-NP identification and quantification more challenging.

Transmission electron microscope equipped with energy dispersive spectroscopy (TEM-EDS) is a routine method for identifying nanoparticles in soil. It could deliver information on the size and chemical composition of nanoparticles from TEM images, but it requires high mercury concentration to obtain reliable results and only provide qualitative information of local areas (such as micron range). As a result, it is unable to provide information about particle number and mass concentrations or is not suitable to quantify nanoparticulate mercury in natural soils. Although synchrotron-based X-ray absorption spectroscopy could identify the speciation of mercury in soils with high mercury concentration (over hundred $mg \cdot kg^{-1}$), it fails to provide the information about size distribution and concentrations of nanoparticulate mercury.

Overall, it is urgent to develop a method for simultaneous and accurate determination of particle size distribution and concentration of Hg-NPs in natural soils.

SUMMARY

In view of this, an object of the present disclosure is to provide a method for simultaneous determination of particle size distribution and concentration of nanoparticulate mercury (Hg-NPs) in natural soils.

In order to achieve the above object, the present disclosure provides the following technical solutions:

Provided is a method for simultaneous determination of particle size distribution and concentration of nanoparticulate mercury in natural soils, including the following steps:

mixing a soil sample with a sodium pyrophosphate solution ("TSPP") and subjecting the resulting mixture to an extraction to obtain a soil mixture;

leaving the soil mixture for a sedimentation and collecting the supernatant for testing; and testing the supernatant using single particle inductively coupled plasma-mass spectrometry ("spICP-MS") to simultaneously obtain the particle size distribution and concentration of nanoparticulate mercury in the soil sample, wherein the mixing includes a first vortex treatment and a shaking treatment performed in sequence; and the extraction includes an ultrasonic treatment and a second vortex treatment performed in sequence.

In some embodiments, a ratio of the soil sample to sodium pyrophosphate is in the range of (0.495-0.505) g: 0.1 mmol, preferably 0.5 g: 0.1 mmol.

In some embodiments, the soil sample is able to pass through a 100-mesh screen. In some embodiments, the soil sample is air-dried before being mixed with the sodium pyrophosphate solution. In the present disclosure, there is no specific limitation on the air-drying operation, and technical means that are well known to those skilled in the art may be used.

In some embodiments, the sodium pyrophosphate solution is at a concentration of 10 mmol/L. In some embodiments, a solvent of the sodium pyrophosphate solution is water, preferably ultrapure water.

In some embodiments, the first vortex treatment is performed at a rotation speed of 2000-2500 rpm for 10-15 s. In some embodiments, the first vortex treatment is performed on a vortex instrument.

In some embodiments, the shaking treatment is performed at a temperature of 24.5-25.5° C., preferably 25° C. In some embodiments, the shaking treatment is performed at a rotation speed of 190-210 rpm, preferably 200 rpm. In some embodiments, the shaking treatment is performed for 30-70 min, preferably 60-70 min. In some embodiments, the shaking treatment is performed in a constant temperature shaking incubator.

In some embodiments, the ultrasonic treatment is performed with an ultrasonic frequency of 40-50 kHz. In some embodiments, the ultrasonic treatment is performed for 14-16 min, and preferably 15 min.

In some embodiments, the second vortex treatment is performed at a rotation speed of 2000-2500 rpm for 10-15 s. In some embodiments, the second vortex treatment is performed on a vortex instrument.

In some embodiments, the soil mixture is left to sediment for 2-3 h.

In some embodiments, after collecting the supernatant, the method includes further diluting the supernatant, the purpose of which is to dilute the Hg-NPs to a concentration that could be accurately determined by spICP-MS. In some embodiments, the concentration that could be accurately determined is in the range of 1-20 ng/L. Since the concentration of Hg-NPs in the soil sample is unknown before determination, in some embodiments the dilution operation is performed by those skilled in the art according to experience. In some embodiments, the supernatant is diluted to a minimum factor of 100. For soil samples with a high Hg-NP concentration, the supernatant needs to be diluted to a higher factor until its concentration could be accurately determined. For embodiments where the dilution is included, the method further includes an ultrasonic treatment after the dilution. In some embodiments, the ultrasonic treatment is performed with an ultrasonic frequency of 50 kHz for 1-5 min.

In the present disclosure, the extraction is to fully separate Hg-NPs from the soil components.

In some embodiments, parameters of spICP-MS determination are shown in Table 1.

In some embodiments of the present disclosure, the spICP-MS determination is performed on spICP-MS.

In some embodiments of the present disclosure, the sampling system of the spICP-MS is subjected to a washing after each test. In the present disclosure, the washing includes a washing with mixed acid, a washing with nitric acid and a washing with water performed in sequence. In some embodiments of the present disclosure, a reagent for the washing with mixed acid is a mixture of hydrochloric acid (2 wt %) and nitric acid (2 wt %) in a volume ratio of 1:1. In some embodiments of the present disclosure, a reagent for the washing with nitric acid is 2 wt % nitric acid. In some embodiments of the present disclosure, a reagent for the washing with water is ultrapure water.

In the present disclosure, washing the sampling system of the spICP-MS could avoid the adsorption of Hg-NPs by the instrument in order to improve the determination accuracy.

In the present disclosure, the concentration of Hg-NPs in the soil sample includes the mass and number concentrations. In the present disclosure, the particle number concentration is the number of Hg-NPs in a sample to be tested, and the mass concentration is the mass of Hg-NPs in a sample to be tested.

The method according to the present disclosure allows quick extraction of Hg-NPs in the soil without dissolution or aggregation, in combination with spICP-MS determination, and makes it possible to realize the simultaneous and accurate determination of the particle size distribution and concentration of Hg-NPs in the complex soil matrix. Moreover, it is simple to operate, feasible to control, and has a wide applicable range, and could be applied to the extraction and determination of Hg-NPs in different soils. Further, the method of the present disclosure requires sample in a small amount, and has a low limit of detection, and is thus suitable for the determination of environmental samples.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DETAILED DESCRIPTION OF THE EMBODIMENTS

The method for simultaneous determination of the particle size distribution and concentration of Hg-NPs in natural soils according to the present disclosure is described in more detail by the examples below; however, these examples do not limit the scope of the present disclosure in any way.

Example 1

Verification of Accuracy

An appropriate amount of synthesized Hg-NPs was weighed and dispersed in ultrapure water to obtain a standard suspension of Hg-NPs.

Figure 1:
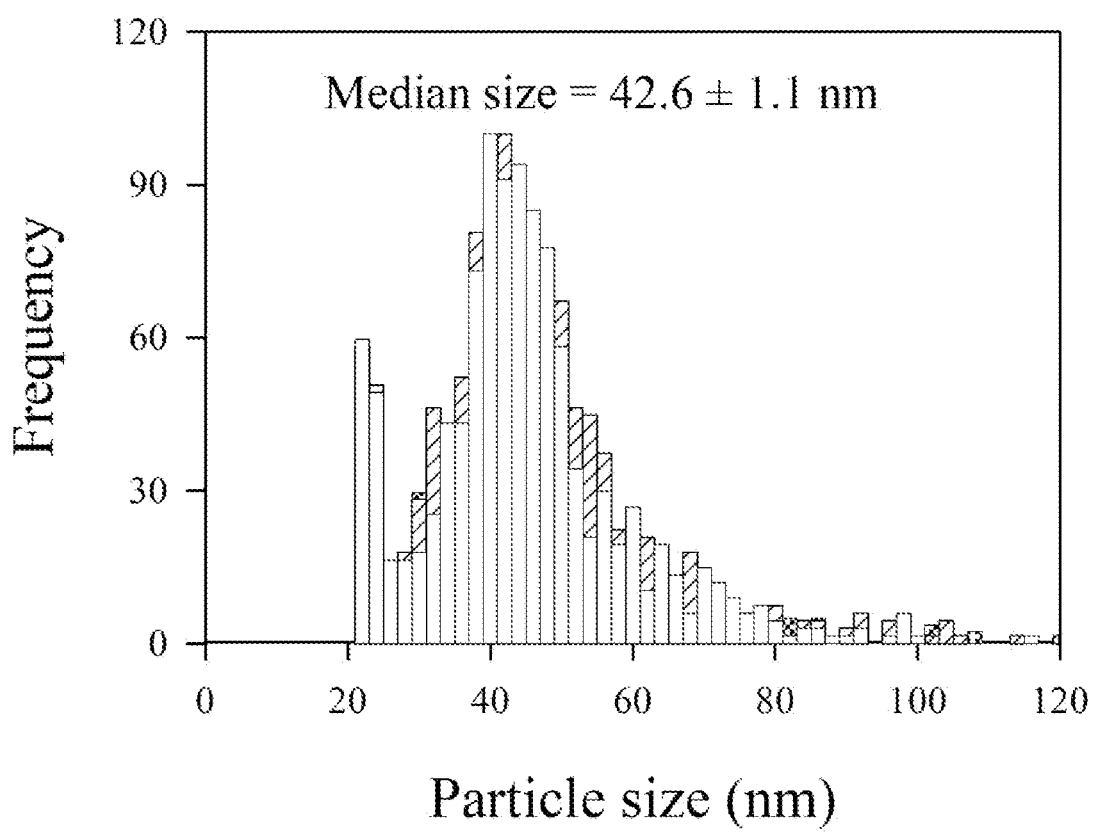
FIG. 1 shows the particle size distribution of synthesized Hg-NPs obtained by spICP-MS.
Figure 2:
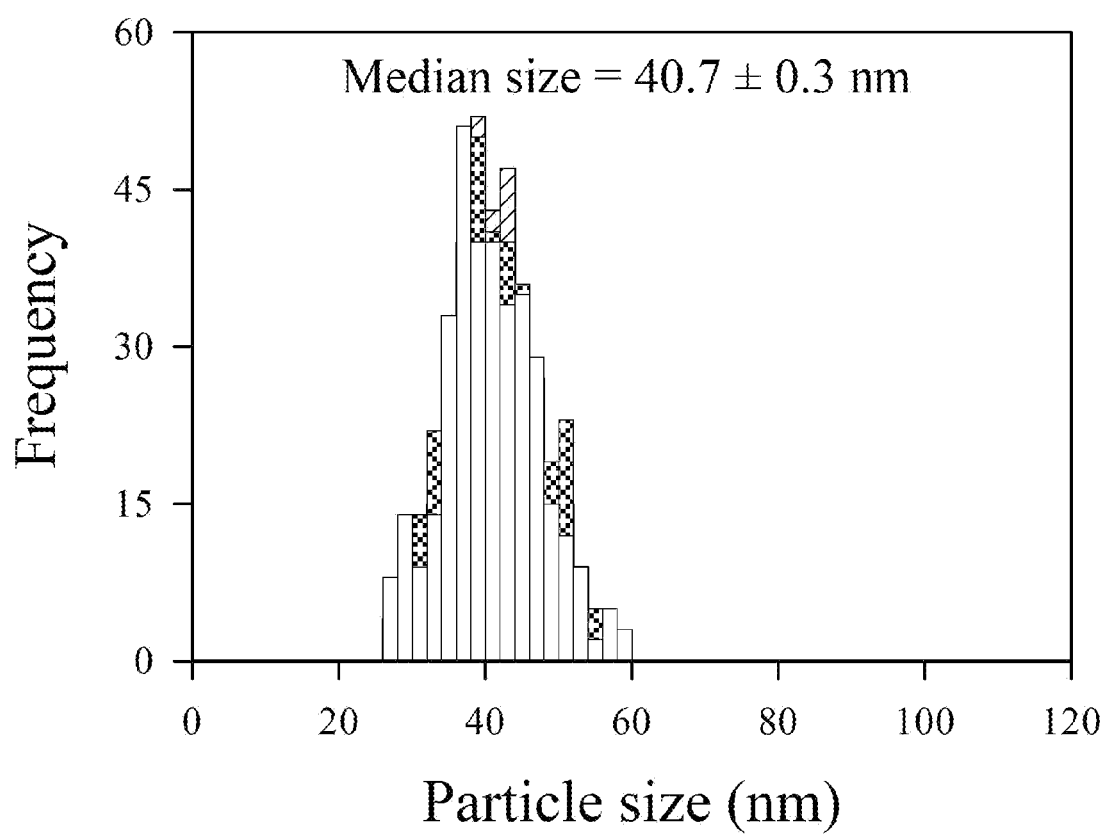
FIG. 2 shows the particle size distribution of synthesized Hg-NPs obtained by TEM-EDS.

The standard suspension of Hg-NPs was subjected to spICP-MS determination and transmission electron microscope equipped with energy dispersive energy spectroscopy (TEM-EDS) determination, to obtain the particle size distribution. The results are shown in FIGS. 1-2. FIG. 1 shows the particle size distribution obtained by spICP-MS, and FIG. 2 shows the particle size distribution obtained by TEM-EDS. There is no significant difference between the particle size distribution of Hg-NPs measured by the two methods, indicating that the particle size distribution of Hg-NPs could be accurately determined by spICP-MS.

Figure 3:
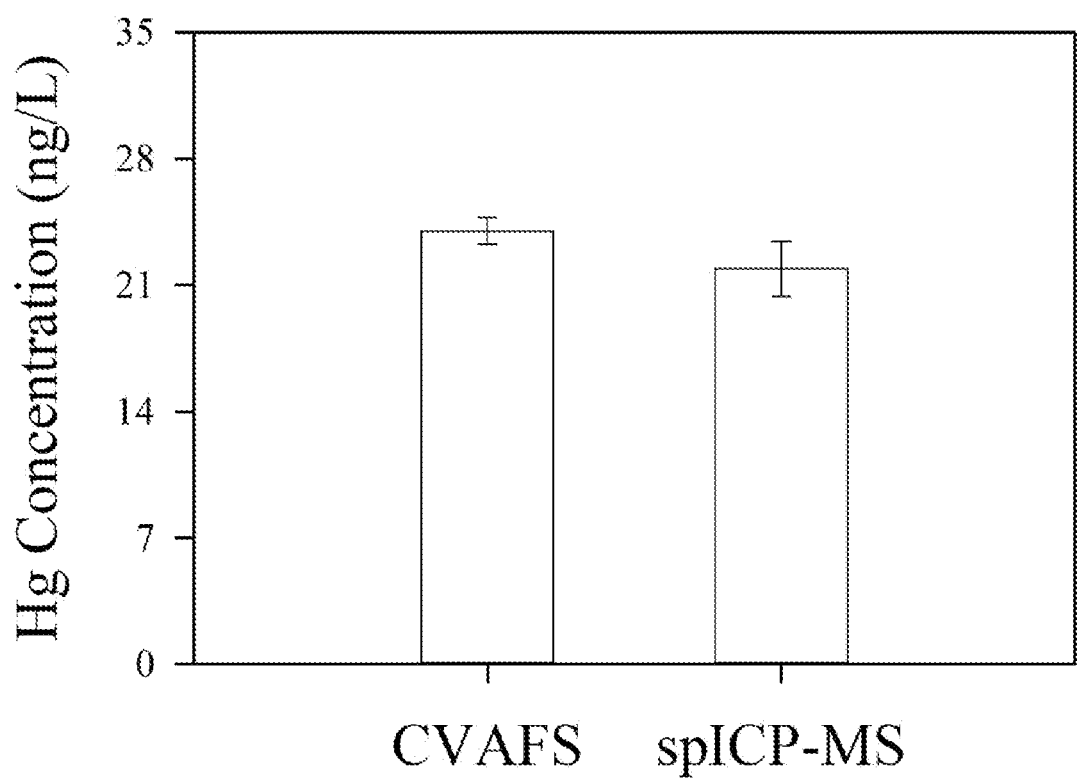
FIG. 3 shows the particle mass concentration of Hg-NPs in the Hg-NP standard solution measured by CVAFS and spICP-MS.

The mass concentration of Hg-NPs in the standard suspension of Hg-NPs was measured by cold-vapor atomic fluorescence spectrometry ("CVAFS") and spICP-MS respectively. FIG. 3 shows that there is no significant difference between the results of mass concentration of Hg-NPs obtained by CVAFS and spICP-MS. This demonstrates that the mass concentration of Hg-NPs could be accurately determined by spICP-MS.

Example 2

2.1 Soil Aging 0.5 g of air-dried soil, passing through a 100-mesh screen, was weighed and placed in a 50 mL centrifuge tube.

100 μL of ultrapure water was added into soil to serve as the control group. 100 μL of a standard suspension of Hg-NPs was spiked into the soil to serve as the experimental group. All groups were vortexed at 2000 rpm for 10 s and then aged at room temperature for 24 h, obtaining aged soil.

2.2 Effect of Different Extractants (1) The aged soil obtained in 2.1 was sampled and extracted by different extractants, including 0.5 mM sodium pyrophosphate (TSPP) solution, 0.5 mM sodium thiosulfate ($Na_2S_2O_3$) solution, 0.5 mM 2,3-dimercaptopropanesulfonic acid sodium salt (DMPS) solution and ultrapure water ($H_2O$). 10 mL of the above extractants were added to the aged soil, and were mixed on a vortex instrument for 10 s (2000 rpm).

(2) The soil mixture obtained in step (1) was shaken at 200 rpm for 70 min (25° C.).

(3) The soil mixture obtained in step (2) was subjected to an ultrasonic treatment (40 kHz, 15 min), and then mixed on a vortex instrument at 2000 rpm for 10 s to obtain a soil mixture.

(4) The soil mixture obtained in step (3) was left to sediment for 2 h at room temperature to allow for the large soil particles settling down in the soil mixture.

(5) The supernatant (100 μL) obtained in step (4) was sampled, diluted with ultrapure water and subjected to spICP-MS analysis for Hg-NP quantification according to the parameters in Table 1.

TABLE 1

Parameters of the single particle inductively coupled plasma-mass spectrometry.

| Instrument parameters | Values |
| --- | --- |
| Radio frequency power | 1600 W |
| Radio frequency matching | 1.84 V |
| Nebulizer gas flow rate | 1 L/min |
| Nebulizer pump rotation speed | 0.1 rps |
| Plasma gas flow rate | 15 L/min |
| Transport efficiency | 4-6% |
| Sample flow rate | 0.25-0.35 mL/min |
| Dwell time | 3 ms |
| Acquisition time | 60-120 s |

Figure 4:
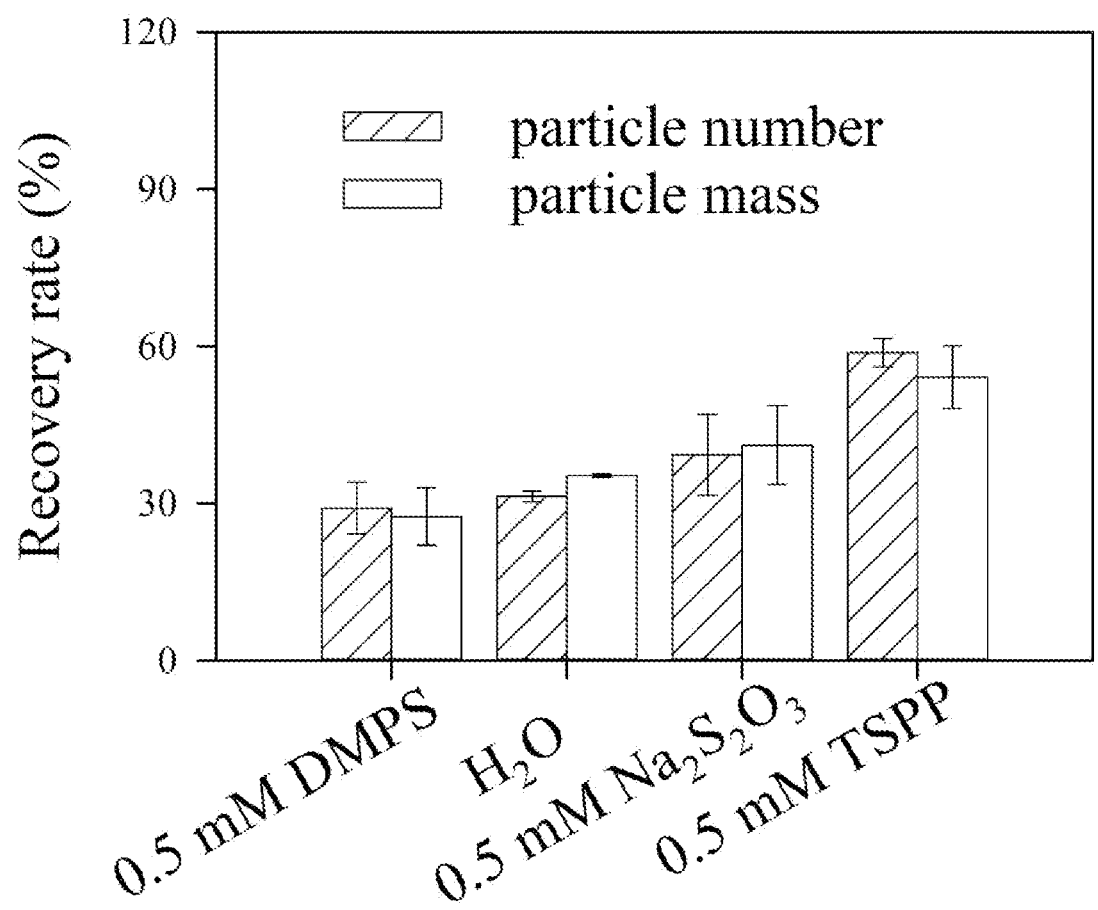
FIG. 4 shows the concentration recovery rates of spiked Hg-NPs in soil using different extractants.

The concentration recovery rates of spiked Hg-NPs in soil using different extractants are shown in FIG. 4. The extraction efficiency is significantly influenced by different extractants. TSPP is the most efficient extractants as compared with others.

2.3 Effect of Different Shaking Time (1) 20 mL of 2.5 mM TSPP solution was used to extract Hg-NPs in the aged soil obtained in 2.1. They were mixed on a vortex instrument for 10 s (2000 rpm).

(2) The soil mixture in step (1) was shaken at 200 rpm (25° C.) for 30 min or 70 min, respectively.

(3) The operation of step (3) in 2.2 was repeated.

(4) The operation of step (4) in 2.2 was repeated.

(5) The operation of step (5) in 2.2 was repeated.

Figure 5:
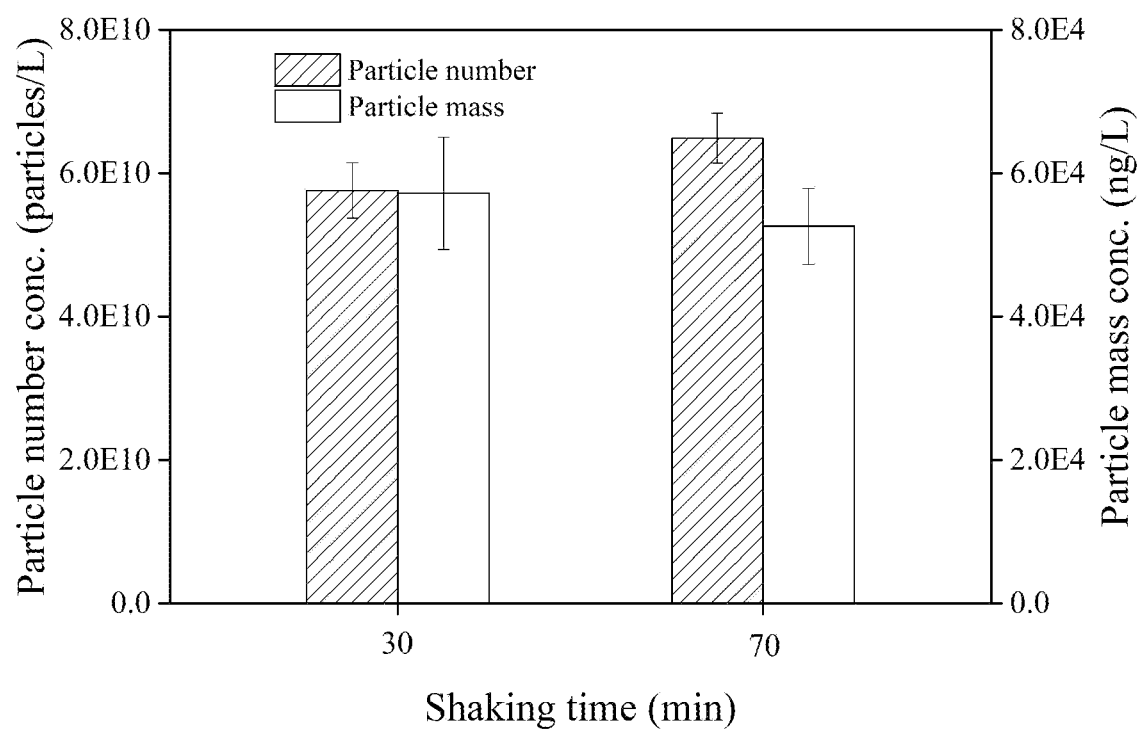
FIG. 5 shows the measured concentrations of spiked Hg-NPs in soil using different shaking time.

The results are shown in FIG. 5. The extraction efficiency is significantly influenced by different shaking time. Compared with the shaking time of 30 min, greater concentrations of Hg-NPs were obtained after shaking for 70 min.

2.4 Effect of Different Ultrasonic Frequencies (1) The operation of step (1) in 2.3 was repeated.
(2) The operation of step (2) in 2.2 was repeated.
(3) The soil mixture obtained in step (2) was subjected to an ultrasonic treatment with a frequency of 40 kHz or 50 kHz for 15 min, and then mixed on a vortex instrument at 2000 rpm for 10 s.
(4) The operation of step (4) in 2.2 was repeated.
(5) The operation of step (5) in 2.2 was repeated.

Figure 6:
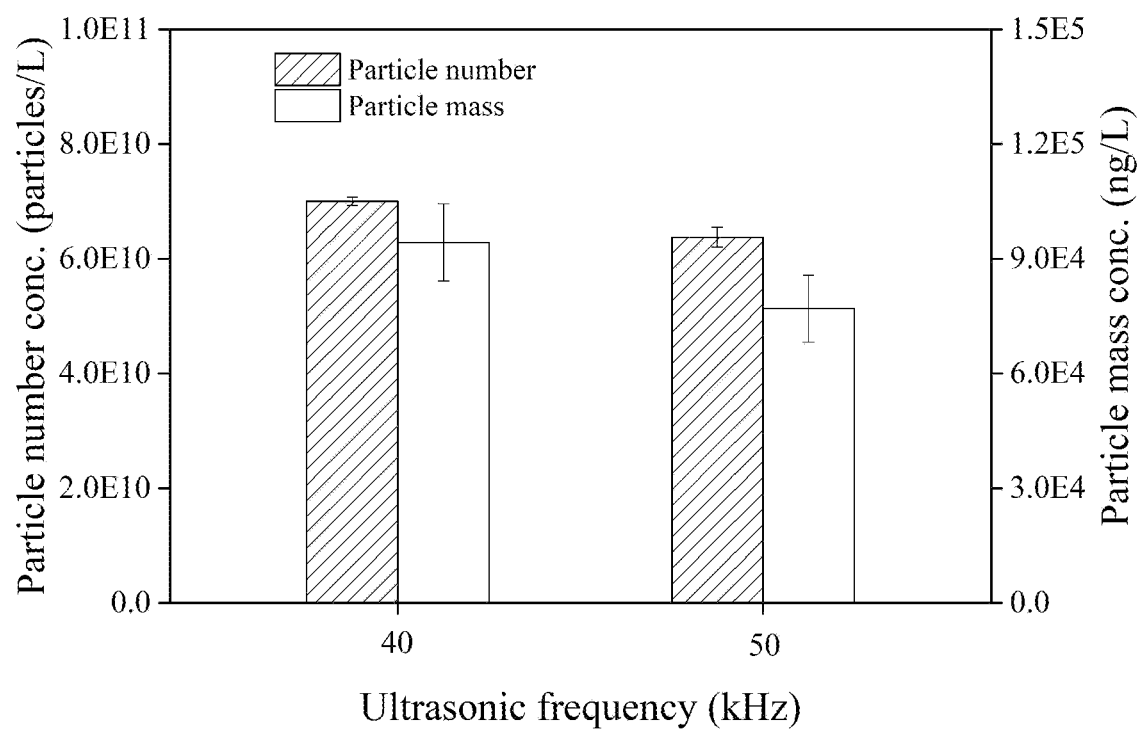
FIG. 6 shows the measured concentrations of spiked Hg-NPs in soil using different ultrasonic frequency.

The results are shown in FIG. 6. The extraction efficiency is significantly influenced by different ultrasonic frequencies. Compared with the ultrasonic frequency of 50 kHz, greater concentrations of Hg-NPs were obtained at a frequency of 40 kHz.

2.5 Effect of Different Sedimentation Time (1) The operation of step (1) in 2.3 was repeated.
(2) The operation of step (2) in 2.2 was repeated.
(3) The operation of step (3) in 2.2 was repeated.
(4) The soil mixture obtained in step (3) was left to sediment for 2 h, 4 h, 6 h and 8 h at room temperature to allow for the large soil particles settling down in the soil mixture.
(5) The operation of step (5) in 2.2 was repeated.

Figure 7:
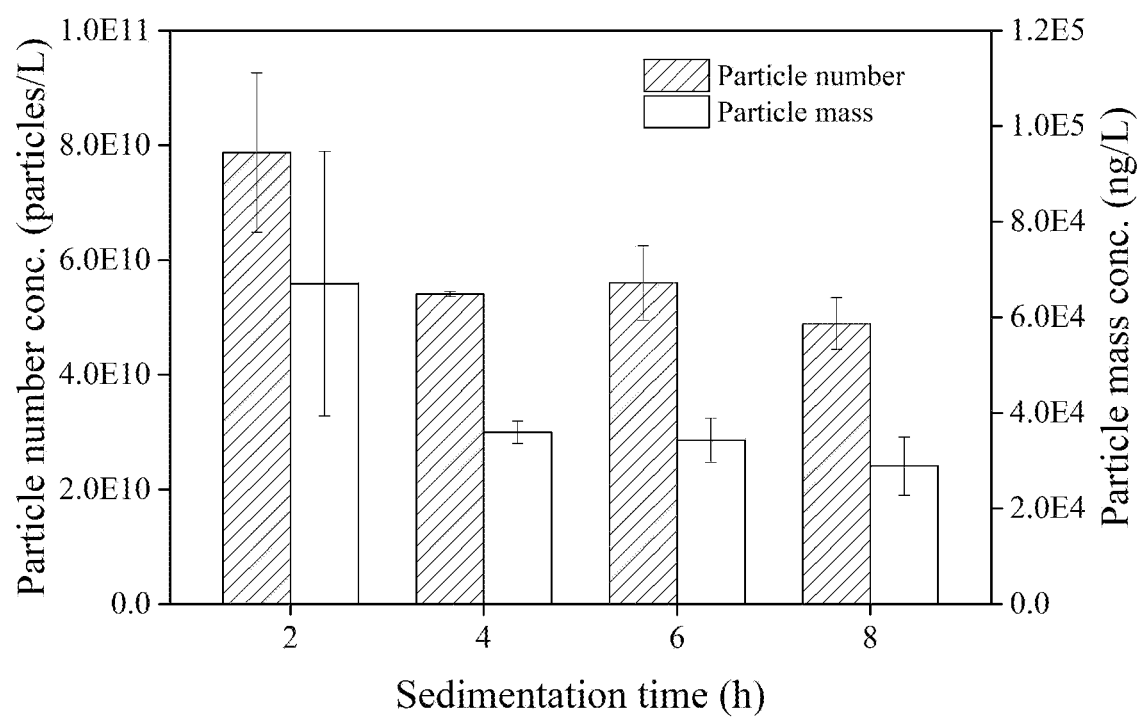
FIG. 7 shows the measured concentrations of spiked Hg-NPs in soil using different sedimentation time.

The results are shown in FIG. 7. The extraction efficiency is significantly influenced by different sedimentation time. The greatest concentration of Hg-NPs was obtained after sedimentation for 2 h.

2.6 Effect of Different Ratios of Soil to Extractant (1) 10 mL, 20 mL, 30 mL and 40 mL of 2.5 mM TSPP solution were added to the aged soil in 2.1, corresponding to soil-to-extractant ratios (g:mL) of 1:20, 1:40, 1:60, and 1:80, respectively, and they were mixed on a vortex instrument for 10 s (2000 rpm).
(2) The operation of step (2) in 2.2 was repeated.
(3) The operation of step (3) in 2.2 was repeated.
(4) The operation of step (4) in 2.2 was repeated.
(5) The operation of step (5) in 2.2 was repeated.

Figure 8:
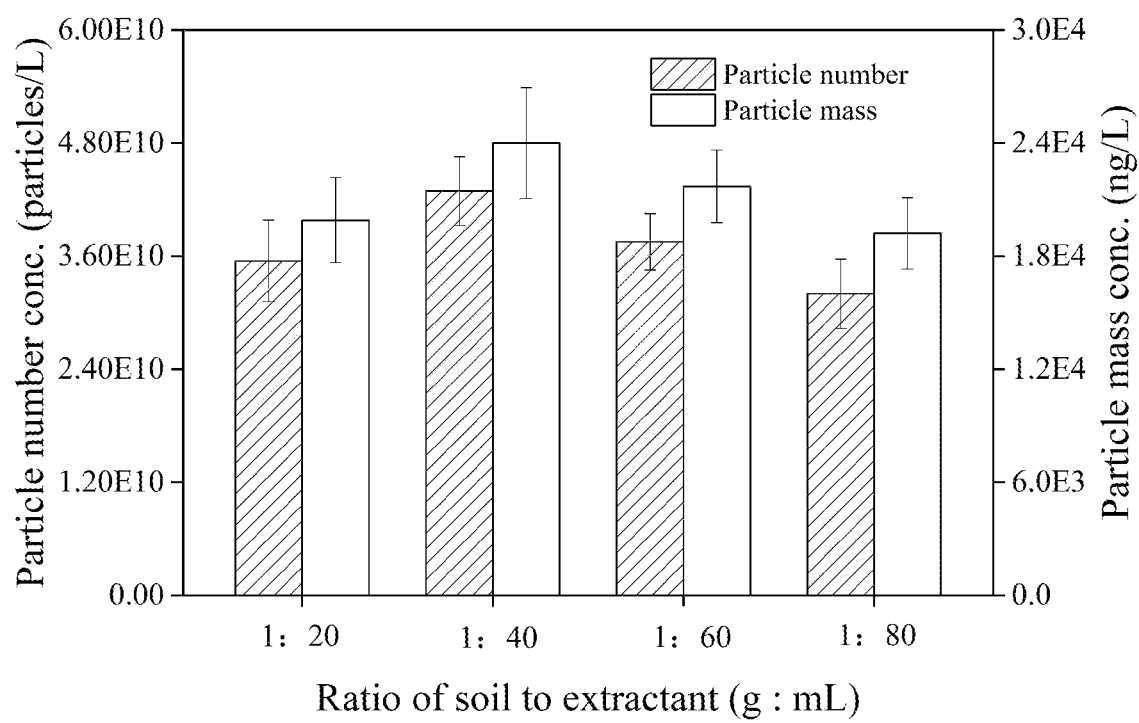
FIG. 8 shows the measured concentrations of spiked Hg-NPs in soil using different ratios of soil to extractant.

The results are shown in FIG. 8. The extraction efficiency is limitedly affected by different ratios of soil to extractant. In order to save raw materials, 10 mL of TSPP, corresponding to a ratio of 1:20, was finally selected for subsequent extraction.

2.7 Effect of TSPP Concentrations (1) The aged soil in 2.1 was sampled and incubated with 10 mL of TSPP at different concentrations, including 0.05 mM, 0.5 mM, 2.5 mM, 10 mM, and 20 mM. They were mixed on a vortex instrument for 10 s (2000 rpm).
(2) The operation of step (2) in 2.2 was repeated.
(3) The operation of step (3) in 2.2 was repeated.
(4) The operation of step (4) in 2.2 was repeated.
(5) The operation of step (5) in 2.2 was repeated.

Figure 9:
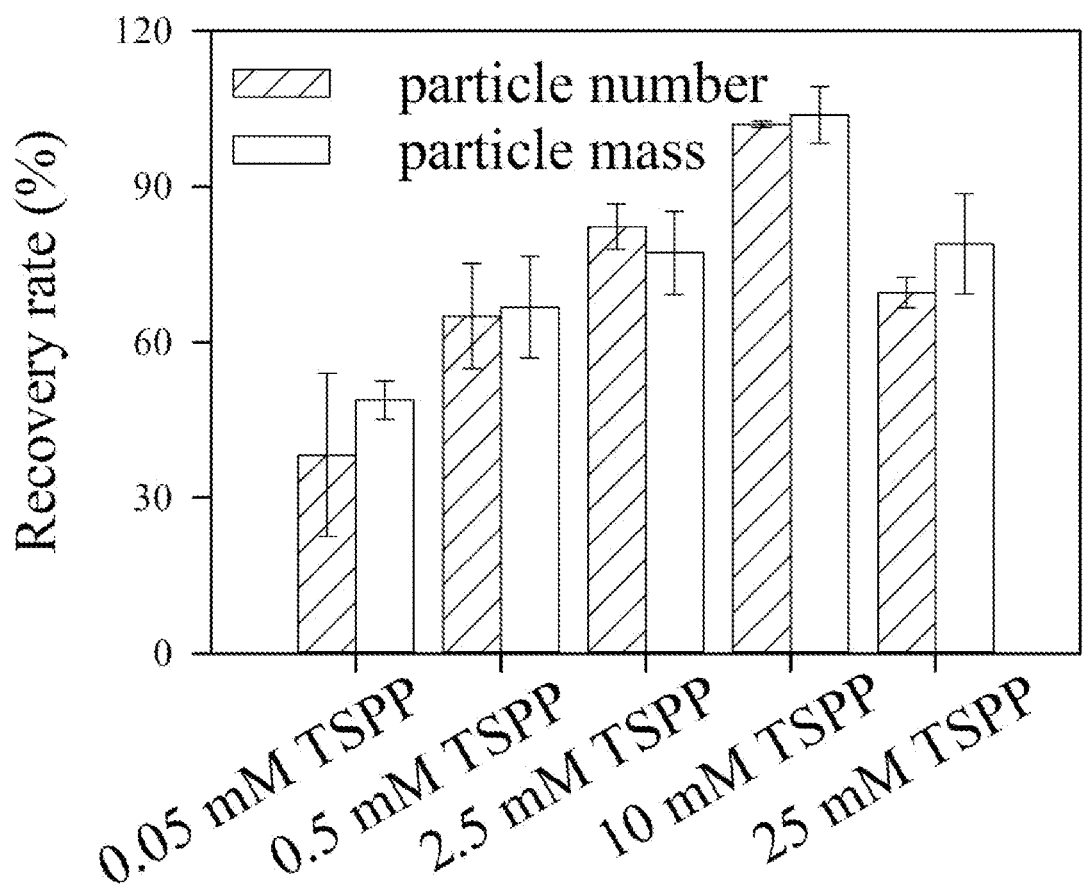
FIG. 9 shows the concentration recovery rates of spiked Hg-NPs in soil using different TSPP concentrations.

The results are shown in FIG. 9. The extraction efficiency is significantly influenced by different TSPP concentrations. The greatest extraction efficiency (95-105%) was obtained at 10 mM TSPP.

Figure 10:
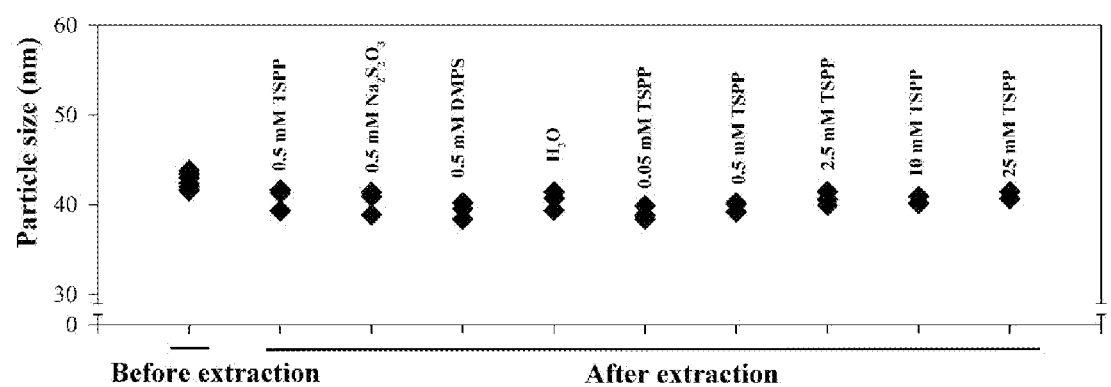
FIG. 10 shows the particle size of spiked Hg-NPs in soils before and after extraction.

The particle size of spiked Hg-NPs in soil before and after extraction using different extractants and different TSPP concentrations are shown in FIG. 10. Particle size of Hg-NPs did not change significantly after extraction.

2.8 Verification of the Method (1) 10 mL of 10 mM TSPP solution was added to the aged soil obtained in 2.1, and then they were mixed on a vortex instrument at 2000 rpm for 10 s.
(2) The operation of step (2) in 2.2 was repeated.
(3) The operation of step (3) in 2.2 was repeated.
(4) The operation of step (4) in 2.2 was repeated.
(5) The operation of step (5) in 2.2 was repeated.

The concentration recovery rates of spiked Hg-NPs were calculated according to Equation 1:

$$\text{Recovery rate} = \frac{CE - CB}{CO} \times 100\% \qquad \text{(Equation 1)}$$

in which CE represents the measured mass/number concentration of spiked Hg-NPs in the experimental group, CB represents the measured mass/number concentration of indigenous Hg-NPs in the control group without Hg-NPs spiking, and CO represents the mass/number concentration of pristine Hg-NPs spiked into the soil.

Figure 11:
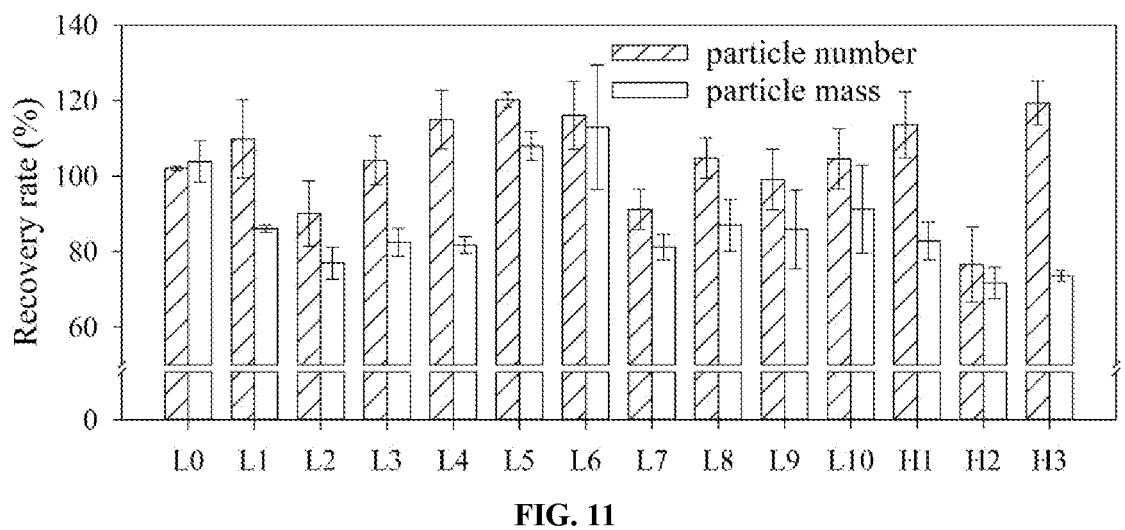
FIG. 11 shows the concentration recovery rates of spiked Hg-NPs in different soils with a wide range of properties.
Figure 12:
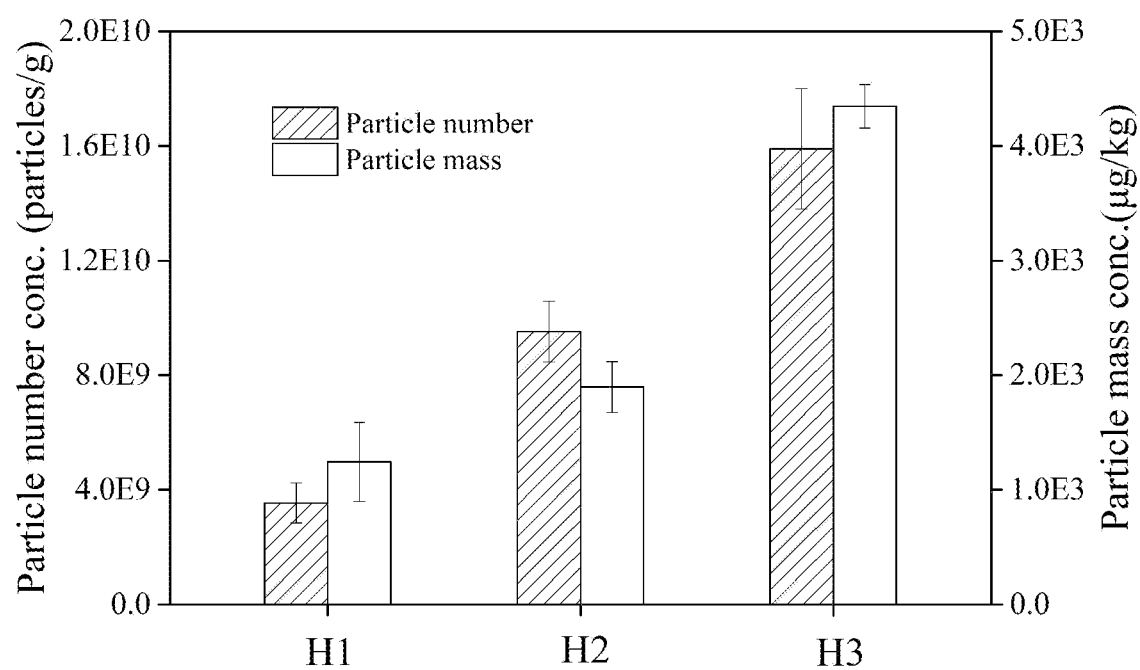
FIG. 12 shows the concentrations of indigenous Hg-NPs in soils H1, H2 and H3.
Figure 13:
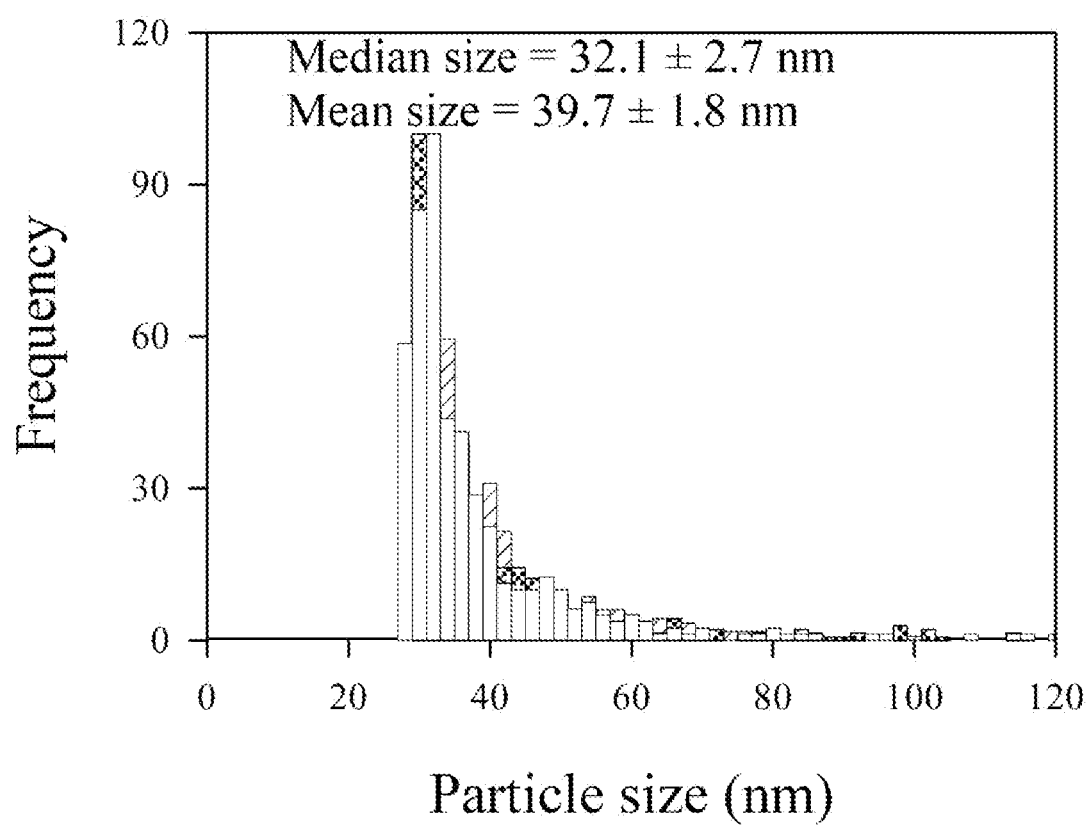
FIG. 13 shows the particle size distribution of indigenous Hg-NPs in soil H1.
Figure 14:
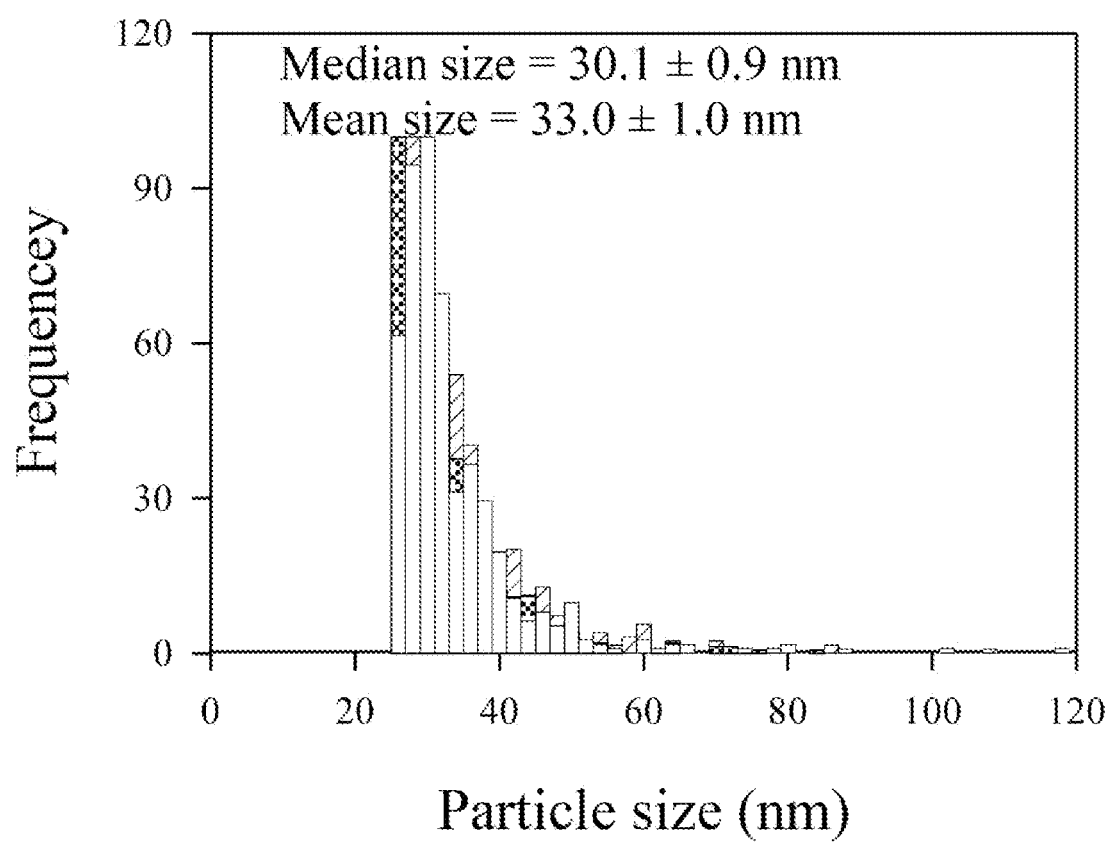
FIG. 14 shows the particle size distribution of indigenous Hg-NPs in soil H2.
Figure 15:
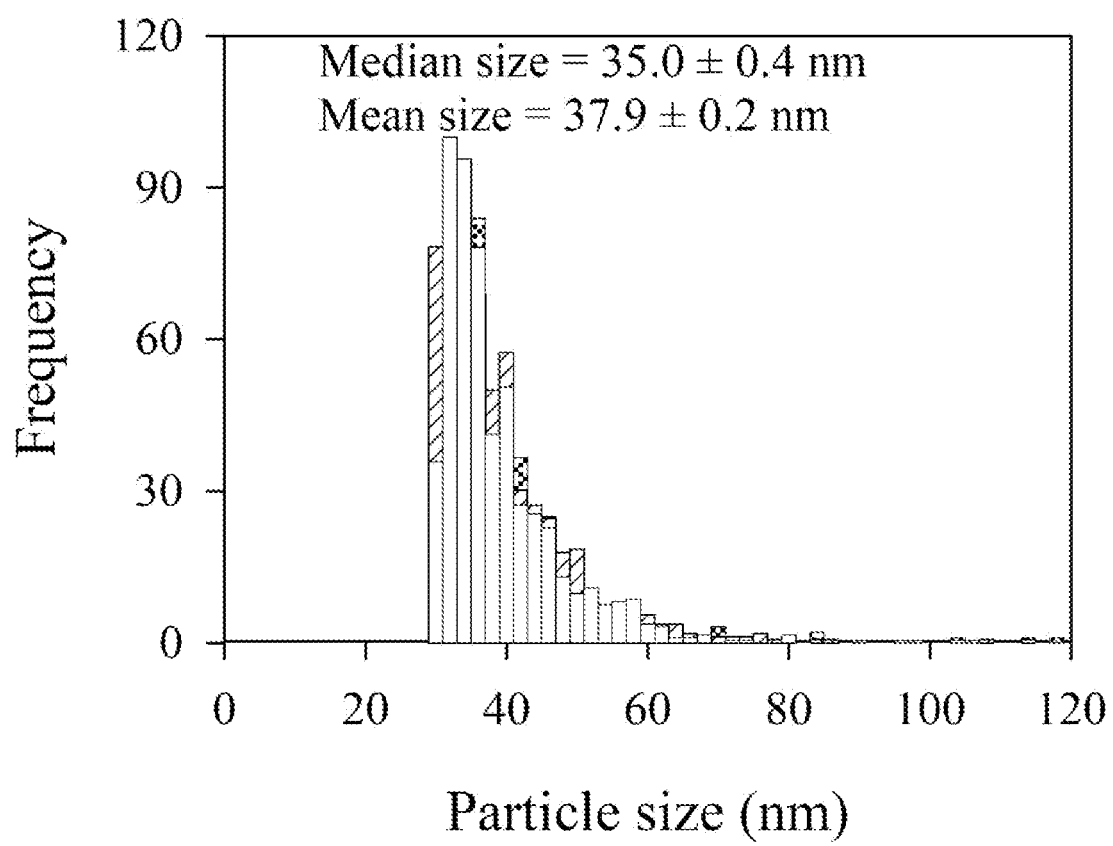
FIG. 15 shows the particle size distribution of indigenous Hg-NPs in soil H3.

The concentration recovery rates of spiked Hg-NPs are examined in fourteen soil samples (soils L0-L10 and H1-H3) and shown in FIG. 11. FIG. 11 shows that the recovery rates of spiked Hg-NPs range from 75% to 120%. Fourteen soil samples have different physical and chemical properties, and three of them (H1-H3) are soils sourced from mercury mining areas. The above results show that the method could be applied to different soils.

In addition, the particle size distribution and concentration of indigenous Hg-NPs in soils H1, H2 and H3 could be obtained at the same time. The results are shown in FIGS. 12-15. FIGS. 12-15 show that the mass concentrations of indigenous Hg-NPs in soils H1, H2, and H3 are 1243.6±344.9, 1896.1±223.8 and 4346.6±189.2 μg/kg, respectively, and the particle number concentrations are (3.5±0.7)×10$^9$, (9.5±1.1)×10$^9$ and (1.6±0.2)×10$^{10}$ particles/g, respectively. In these three soils, indigenous Hg-NPs has a median size of about 30 nm (32.1±2.7, 30.1±0.4 and 35.0±0.4 nm for soil H1, H2, and H3, respectively).

Example 3

Detection Limit of the Method

The particle size detection limit (SDL) of Hg-NPs by spICP-MS was calculated according to Equation 2:

$$SDL = \left(\frac{6 \times I_L}{\pi \times 10^{-6} \times \rho \times S_m \times f_a}\right)^{1/3} \qquad \text{(Equation 2)}$$

In Equation 2, $S_m = S/(V_s \times \eta)$, $I_L$ represents the background signal (counts), p represents the density of HgS (g/cm$^3$), $f_a$ represents the mass fraction of Hg in HgS, and S represents the sensitivity of the instrument to Hg (cps L/ng), $V_s$ represents the sample flow rate of spICP-MS (μL/s), and η represents the transport efficiency.

Therefore, the particle size detection limit of Hg-NPs measured by spICP-MS was 21 nm.

The limit of detection (LOD) of particle number concentration of Hg-NPs by spICP-MS was calculated according to Equation 3:

$$LOD = \frac{3}{\eta \times V_s \times t_i} \qquad \text{(Equation 3)}$$

In Equation 3, $t_i$ represents the acquisition time (s).

Therefore, the limit of detection of particle number concentration of Hg-NPs by spICP-MS was calculated to be 1.2×10$^5$ particles/L.

The above are only the preferred embodiments of the present disclosure. It should be pointed out that for those of ordinary skill in the art, without departing from the principle of the present disclosure, several improvements and modifications could be made, and these improvements and modifications should fall within the scope of the present disclosure.

What is claimed is:

1. A method for simultaneous determination of particle size distribution and concentration of nanoparticulate mercury in natural soils, comprising
    mixing a soil sample with a sodium pyrophosphate solution (TSPP) and subjecting the resulting mixture to an extraction to obtain a soil mixture;
    leaving the soil mixture for a sedimentation and collecting a supernatant for testing; and
    testing the supernatant using single particle inductively coupled plasma-mass spectrometry (spICP-MS) to simultaneously obtain the particle size distribution and concentration of nanoparticulate mercury in the soil sample;
    wherein the mixing includes a first vortex treatment and a shaking treatment performed in sequence;
    the extraction includes an ultrasonic treatment and a second vortex treatment performed in sequence.

2. The method as claimed in claim 1, wherein a ratio of the soil sample to sodium pyrophosphate is in the range of (0.495-0.505) g: 0.1 mmol.

3. The method as claimed in claim 2, wherein the soil sample is able to pass through a 100-mesh screen.

4. The method as claimed in claim 2, wherein the sodium pyrophosphate solution has a concentration of 10 mmol/L.

5. The method as claimed in claim 1, wherein the soil sample is able to pass through a 100-mesh screen.

6. The method as claimed in claim 1, wherein the sodium pyrophosphate solution is at a concentration of 10 mmol/L.

7. The method as claimed in claim 1, wherein the first vortex treatment is performed at a rotation speed of 2000-2500 rpm for 10-15 s.

8. The method as claimed in claim 1, wherein the shaking treatment is performed at a temperature of 24.5-25.5° C. and a rotation speed of 190-210 rpm for 30-70 min.

9. The method as claimed in claim 1, wherein the ultrasonic treatment is performed with an ultrasonic frequency of 40-50 kHz for 14-16 min.

10. The method as claimed in claim 1, wherein the second vortex treatment is performed at a rotation speed of 2000-2500 rpm for 10-15 s.

11. The method as claimed in claim 1, wherein the soil mixture is left to sediment for 2-3 h.

12. The method as claimed in claim 1, wherein parameters of the single particle inductively coupled plasma-mass spectrometry are shown as follows:

| | |
|---|---|
| radio frequency power: | 1600 W |
| radio frequency matching: | 1.84 V |
| nebulizer gas flow rate: | 1 L/min |
| nebulizer pump rotation speed: | 0.1 rps |
| plasma gas flow rate: | 15 L/min |
| transport efficiency: | 4-6% |
| sample flow rate: | 0.25-0.35 mL/min |
| dwell time: | 3 ms |
| acquisition time: | 60-120 s |

\* \* \* \* \*